United States Patent [19]

Cobb

[11] Patent Number: 4,480,142
[45] Date of Patent: Oct. 30, 1984

[54] CATALYTIC ALKYLATION

[75] Inventor: Raymond L. Cobb, Bartlesville, Okla.

[73] Assignee: Phillips Petroleum Co., Bartlesville, Okla.

[21] Appl. No.: 439,004

[22] Filed: Nov. 4, 1982

[51] Int. Cl.³ .............................................. C07C 2/68
[52] U.S. Cl. ................................... 585/465; 585/458; 585/466; 585/468
[58] Field of Search ............... 585/458, 465, 466, 468

[56] References Cited

U.S. PATENT DOCUMENTS

| 2,471,922 | 5/1949 | Axe | 260/671 |
|---|---|---|---|
| 2,564,488 | 8/1951 | Mahan | 260/671 |
| 3,435,091 | 3/1969 | Hofmann et al. | 585/465 |
| 3,849,507 | 11/1974 | Zuech | 260/671 |
| 4,165,440 | 8/1979 | Kim | 568/867 |
| 4,316,997 | 2/1982 | Vaughan | 585/458 |

OTHER PUBLICATIONS

*Chemical Abstracts* pars.: 44:106906 (1950), 59:151956 (1962), 63:5544C (1965), 75:758876 (1971), and 76:72197M (1972).

*Primary Examiner*—Curtis R. Davis
*Attorney, Agent, or Firm*—Howard D. Doescher

[57] ABSTRACT

The alkylation of aromatic compounds with olefins can be conducted more efficiently in the presence of certain catalysts.

13 Claims, No Drawings

CATALYTIC ALKYLATION

BACKGROUND

The alkylation of biphenyls or other polyphenyls using olefins is a well-known reaction. However, the reactions have usually had low selectivity to the 2-alkyl products, i.e., the 3- and 4-alkyl isomers and disubstituted derivatives were predominant.

Isopropyl-substituted aromatics, such as isopropyl biphenyls, are being considered as replacements for the environmentally-undesirable chlorinated aromatics now being used in the electrical industry. Alkylated aromatics also have utilities as solvents and chemical intermediates.

INVENTION

It has been discovered that the reaction of 1-olefins with bi- or polyphenyl compounds can be carried out more efficiently in the presence of certain catalysts.

In accordance with the invention, biphenyl is reacted with an olefin in the presence of an acid catalyst to produce alkyl-substituted biphenyls, and an improvement is made in product selectivity by selecting reaction conditions with respect to the catalyst type to give as the major product 2-alkylbiphenyls. For example, 2-isopropylbiphenyl is obtained as the major component when a molar ratio of from 0.49:1 to 2.21:1 of propylene to biphenyl is heated in the presence of an acid-treated montmorillonite clay catalyst (Filtrol ®71) at a temperature between 100° to 125° C. The remaining products are the 3- and 4-isomers, as well as the disubstituted derivatives. A $BF_3.H_3PO_4$ catalyst at 70°–75° C. gives mainly 2-isopropylbiphenyl when the propylene:biphenyl ratio is below about 1.69:1.

OBJECTS OF THE INVENTION

It is an object of the invention to produce alkyl-substituted aromatic compounds more efficiently.

It is another object of the invention to provide a catalytic process for the alkylation of aromatic compounds with olefins at moderate temperatures.

ADVANTAGES

Alkylation carried out in accordance with the invention have high selectivities to certain isomers. For instance, in the reaction of propylene with biphenyl, the selectivity to 2-isopropyl biphenyl is generally 45% or more when the catalysts of the invention are employed. Due to the nature of the catalysts, the production of 2-alkyl isomers can be maximized at relatively low temperatures.

Because the catalytic alkylations of the invention have high selectivities to certain products and require lower temperatures than other techniques, they are more efficient, in terms of energy and costs, than other processes.

Other objects and advantages will become apparent from the specification and claims.

DESCRIPTION OF THE INVENTION

Olefins

Olefins useful in this invention are alpha- or 1-olefins represented by the formula

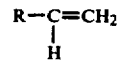

where R can be hydrogen or any alkyl radical having from about 1 to 12 carbon atoms. Suitable olefin reactants include: ethylene, propylene, 1-butene, 3-methyl-1-butene, 3-methyl-1-pentene, 4-methyl-1-pentene, 1-hexene, 1-octene, 1-decene, 1-dodecene, 1-tetradecene, 3-methyl-1-hexene, 3-methyl-2-ethyl-1-hexene, and the like. Mixtures of olefins can be employed.

Aromatic Compounds

Aromatic compounds useful in this invention are those represented by the formula:

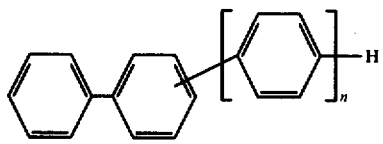

where n can equal 0 or any integer from 1 to about 4. Suitable aromatic compounds include biphenyl, o-, m-, p-terphenyls, quaterphenyls, quinquiphenyls, hexaphenyls, and the like. Mixtures of aromatic reactants can be used.

The mole ratio of olefin to aromatic compound can be any at which substantial alkylation occurs. Generally, olefin/aromatic ratios of about 0.2:1 to about 2.5:1, and preferably less than about 1.7:1, are employed.

Reaction Conditions

While the skilled artisan can readily discern parameters under which alkylation occurs, applicant will make suggestions from which the artisan can extrapolate.

The reaction can be conducted at pressures ranging from 0 to about 100 atmospheres, with the temperature dependent in part on the type of catalyst employed. Typical reaction temperatures will be moderate ones, i.e., between about 65° and 135° C. Generally, when an acid-treated montmorillonite catalyst is used, the reaction temperature will be from about 75° to about 125° C. With a $BF_3$ complex as catalyst, the reaction temperature will generally be from about 50° C. to about 100° C., depending on the volatility and stability of the catalyst employed.

Catalysts

The $BF_3$ complex catalyst is typically a liquid and can be generally any $BF_3$ complex normally used as a catalyst. It can be, for example, but not limited to, such materials as $BF_3.H_3PO_4$, $BF_3.CH_3COOH$, $BF_3.C_2H_5OC_2H_5$, $BF_3.CH_3OH$, and the like. Mixtures containing these and other $BF_3$ complexes can be used.

The solid acid-treated montmorillonite sub-bentonite clays useful as catalysts in this invention are described by the idealized formula $Al_2Si_4O_{10}(OH_2).nH_2O$. The actual mineral, however, has every sixth aluminum ion replaced by a magnesium ion. This produces a crystal lattice with a negative charge which is neutralized by the absorption of metallic cations on the surface. These surface cations are readily removed; and in the process of activation with acid, hydrogen ions are exchanged for the metallic ions, giving, in effect, a solid acid catalyst. The acid-activated material may be designated a magnesium-substituted hydrogen montmorillonite. The acid treatment further enhances the catalytic activity of the material by removing inactive impurities and exposed additional contact surface. A catalytic material of this type is sold commercially under the trade name of "Filtrol". A typical mineral analysis of such a catalyst is:

| Filtrol Grade 71 | |
|---|---|
| | % |
| $SiO_2$ | 71.2 |
| $Al_2O_3$ | 16.5 |
| MgO | 3.2 |
| $Fe_2O_3$ | 3.6 |
| CaO | 2.6 |
| $SO_3$ | 1.3 |
| $K_2O + Na_2O$ | 1.0 |
| $TiO_2$ | 0.6 |
| Acidity | 5.0–8.0 mg KOH/g |

Montmorillonite clays having acid numbers from 1 to 600, preferably 5 to 400, mg KOH/g are considered to be within the scope of this invention.

The preparation of such acid clays is described by B. A. Stagner in "The Science of Petroleum", Vol. III, page 1699 (1938). U.S. Pat. No. 2,564,488 also describes similar montmorillonite clays as herein described. The disclosures of both are incorporated herein by reference.

The perfluoroorganosulfonic acid catalysts used herein are fluorocarbon sulfonic acid resins. Typically, they are produced by copolymerizing fluorinated olefins with perfluorinated olefinic sulfamic acids. After polymerization, the products are treated to yield sulfonic acid polymers. Suitable catalysts and their salts are commercially available under the trademark Nafion ®. One preferred catalyst is made by acidifying Nafion 511 ® with dilute nitric acid. Mixtures of these catalysts can be employed.

Suitable temperatures for the use of perfluoroorganosulfonic acid catalysts in the processes of the invention are about 130° C. to about 200° C., preferably about 150° C. to about 180° C.

While the amount of catalyst used is not critical, and can be readily ascertained by routine experimentation, it is suggested that quantities of broadly about 1 to about 20 grams of catalyst per 100 grams of biphenyl, and preferably about 3 to about 12 grams of catalyst per 100 grams of biphenyl be employed.

EXAMPLES

EXAMPLE I

This example illustrates the activity and selectivity of an acid-treated polymer in alkylating biphenyl with an olefin. This example also serves to illustrate the general procedure for alkylating using various catalysts as herein described.

To a 100 milliliter 4-necked flask fitted with a stirrer, thermometer, condenser and gas inlet tube was charged 25 grams (0.162 mole) of biphenyl and 2 milliliters of Nafion H ® (a copolymer of tetrafluoroethylene and perfluoro-3,6-dioxa-4-methyl-7-octen-sulfonic acid that has been preacidified with dilute $HNO_3$, washed and dried, available from Du Pont. The mixture was stirred and heated to 130° C. under a nitrogen atmosphere. Propylene was added through a calibrated flow meter at 0.25 grams per minute until a total of 12 grams (1.285 moles) had been introduced. The mixture was analyzed by GLC on a 6 ft.×0.25 in. column packed with 10 wt. % General Electric methyl silicone rubber SE-30 on 80×100 mesh Chormosorb W acid washed and dimethylchorosilane treated, programmed from 150° C. to 300° C. at 10 degrees/minute. The run was repeated at 155° C. and 180° C. Analyses were made at various points during the reaction. The results, which are listed in Table I, show that as the conversion of biphenyl increases, the product selectivity, particularly to 2-isopropylbiphenyl, decreases. The results also show that a 50 degree change in reaction temperature does not significantly change selectivity.

TABLE I

ALKYLATION OF BIPHENYL USING PREFLUOROSULFONIC ACID RESIN (NAFION) CATALYST

| Reaction Temp. °C. | $C_3^=/BP^a$ Mole Ratio | % $BP^a$ Conv. | % Selectivity at Various Conversions | | |
|---|---|---|---|---|---|
| | | | 2-$IPBP^a$ | 3-$IPBP^a$ | 4-$IPBP^a$ |
| 130 | 0.86 | <45 | 45 | 10 | 20 |
| 155 | 0.80 | 50 | 42 | 10 | 22 |
| | 1.30 | 75 | 30 | 7 | 18 |
| 180 | 0.78 | 50 | 43 | 14 | 27 |
| | 1.15 | 75 | 33 | 9 | 20 |

$^a$BP is biphenyl
2-IPBP is 2-isopropylbiphenyl
3-IPBP is 3-isopropylbiphenyl
4-IPBP is 4-isopropylbiphenyl
Dialkyl BP is diisopropylbiphenyl which includes all isomers.

EXAMPLE II

This example is the invention and demonstrates the high selectivity to alkylation in the 2-position when using one of the inventive catalysts, Filtrol 71, an acid-treated montmorillonite clay having a acid number of about 8 mg KOH per gram. The procedure described in Example I was repeated except Filtrol 71 (about 8 grams) was used as the catalyst. The results using this catalyst are shown in Table II. The data indicate that when the desired product is the 2-alkylated derivative, it is better to operate at a lower temperature, preferably around 100° C., than higher (e.g., 180°-225° C.) even though the conversion is lower. The data also suggest that when operating at around 100° C. the mole ratio of propylene to biphenyl can vary from 0.3:1 to over 2.0:1 and still give the high 2-substituted product selectivity although biphenyl conversion increases with increased olefin-to-biphenyl ratio.

TABLE II

ALKYLATION OF BIPHENYL USING ACID TREATED MONTMORILLONITE CLAY (FILTROL ®) CATALYST

| Run No. | $C_3^=/BP$ Mole Ratio | % BP Conv. | Rxn Temp. °C. | Selectivity by $GLC^a$ | | | |
|---|---|---|---|---|---|---|---|
| | | | | 2-IPBP | 3-IPBP | 4-IPBP | Dialkyl BP |
| 1 | 1.18 | 68.4 | 225 | 2.2 | 41.9 | 28.0 | 28.1 |
| 2 | 1.16 | 79.1 | 180 | 1.9 | 33.0 | 20.6 | 44.4 |
| 3 | 1.18 | 77.1 | 125 | 38.6 | 11.1 | 13.8 | 36.6 |
| 4 | 1.06 | 30.7 | 100 | 59.4 | 11.6 | 24.2 | 4.8 |

TABLE II-continued
ALKYLATION OF BIPHENYL USING ACID TREATED MONTMORILLONITE CLAY (FILTROL ®) CATALYST

| Run No. | $C_3^=$/BP Mole Ratio | % BP Conv. | Rxn Temp. °C. | Selectivity by GLC[a] | | | |
|---|---|---|---|---|---|---|---|
| | | | | 2-IPBP | 3-IPBP | 4-IPBP | Dialkyl BP |
| 5 | .30 | 4.5 | 100 | 64.8 | 9.7 | 24.7 | — |
| 6 | .49 | 10.1 | 100 | 61.5 | 11.5 | 27.1 | — |
| 7 | .68 | 16.1 | 100 | 59.6 | 11.2 | 27.1 | 2.2 |
| 8 | 1.06 | 30.7 | 100 | 59.4 | 11.6 | 24.2 | 4.8 |
| 9 | 1.44 | 48.8 | 100 | 50.2 | 10.9 | 21.8 | 16.2 |
| 10 | 1.82 | 62.8 | 100 | 45.7 | 10.0 | 18.2 | 24.3 |
| 11 | 2.21 | 72.4 | 100 | 42.2 | 9.9 | 15.8 | 29.8 |

[a] 2-IPBP is 2-isopropylbiphenyl
3-IPBP is 3-isopropylbiphenyl
4-IPBP is 4-isopropylbiphenyl
Dialkyl BP is diisopropylbiphenyl which includes all isomers.

EXAMPLE III

This example is the invention and demonstrates the high selectivity of 2-alkylated products when using another acid catalyst, $BF_3 \cdot H_3PO_4$. The data which is shown in Table III indicates that selectivity to the 2-alkylated biphenyl increases and biphenyl conversion decreases when the mole ratio of olefin-to-biphenyl decreases. Although the reaction was conducted at only two reaction temperatures (70° C. and 75° C.), the limited data suggests a slightly higher 2-alkylated product selectivity when the reaction is conducted at the higher temperature.

EXAMPLE IV

This example is a control that illustrates the performance of various other acid-containing catalysts. The procedure used was that described in Example I. The results given in Table IV show that the selectivity of 2-isopropylbiphenyl, is not as great as it is in the inventive runs, Examples II and III. Table I also shows that materials known to be good alkylation catalysts, such as $AlCl_3$ and $H_2SO_4$ treated catalysts, do not give as good selectivity to the desired 2-alkylated biphenyls as does the instant invention.

TABLE III
ALKYLATION OF BIPHENYL USING $BF_3 \cdot H_3PO_4$ CATALYST

| Run No. | Rxn Temp, °C. | $C_3^=$/BP[a] Mole Ratio | % BP[a] Conv. | 2-IPBP | 3-IPBP | 4-IPBP | Dialkyl BP |
|---|---|---|---|---|---|---|---|
| 1 | 70 | 0.87 | 55.6 | 36.7 | 16.6 | 29.5 | 17.1 |
| 2 | 70 | 1.69 | 90.2 | 31.5 | 12.5 | 26.5 | 29.4 |
| 3 | 70 | 2.57 | 98.0 | 25.1 | 30.2 | | 44.6 |
| 4 | 70 | 3.64 | 100 | 14.3 | 14.9 | | 70.8 |
| 5 | 70 | 3.95 | 100 | 12.9 | 1.2 | 3.9 | 82.0 |
| 6 | 75 | 0.06 | 4.0 | 50.4 | 20.9 | 28.7 | 0 |
| 7 | 75 | 0.24 | 15.4 | 45.5 | 20.0 | 29.3 | 5.2 |
| 8 | 75 | 0.42 | 27.4 | 45.6 | 20.0 | 29.2 | 5.2+ |
| 9 | 75 | 0.60 | 42.3 | 38.9 | 18.5 | 28.8 | 13.7 |
| 10 | 75 | 0.77 | 53.2 | 39.3 | 19.9 | 28.0 | 12.8 |
| 11 | 75 | 0.95 | 64.7 | 38.0 | 20.3 | 26.6 | 15.2 |
| 12 | 75 | 1.13 | 73.4 | 37.3 | 19.1 | 26.6 | 17.1 |
| 13 | 75 | 1.31 | 80.5 | 37.0 | 18.0 | 27.3 | 17.6 |

[a] BP is biphenyl
2-IPBP is 2-isopropylbiphenyl
3-IPBP is 3-isopropylbiphenyl
4-IPBP is 4-isopropylbiphenyl
Dialkyl BP is diisopropylbiphenyl which includes all isomers.

TABLE IV
ALKYLATION OF BIPHENYL USING VARIOUS ACID-TYPE ALKYLATION CATALYSTS

| Run No. | Catalyst | Reaction Temp. °C. | $C_3^=$/BP Mole Ratio | % BP Conv. | % Selectivity at Various Conversions | | |
|---|---|---|---|---|---|---|---|
| | | | | | 2-IPBP | 3-IPBP | 4-IPBP |
| 1 | Silica-Alumina[a] | 150 | 1.45 | 50 | 29 | 15 | 42 |
| | | 150 | 1.90 | 75 | 21 | 10 | 31 |
| | | 180 | 1.10 | 50 | 27 | 15 | 45 |
| 2 | Acid-treated Silica-Alumina[b] | 155 | .52 | 50 | 36 | 11 | 33 |
| | | 180 | .51 | 50 | 32 | 10 | 33 |
| | | 180 | .86 | 75 | 23 | 7 | 25 |
| 3 | Acid-treated Micro-gel[c] | 130 | Little reaction, alkylation too slow | | | | |
| | | 150 | Little reaction, alkylation too slow | | | | |
| | | 180 | .31 | 44 | 35 | 9 | 36 |
| 4 | High Acid Linde Mole Sieve[d] | 100 | 3.9 | 35 | 46 | 18 | 29 |
| | | 130 | 3.9 | 35 | 38 | 20 | 31 |
| 5 | $AlCl_3$ | 80 | .40 | 50 | 0 | 53 | 32 |
| | | 80 | .90 | 75 | 0 | 40 | 25 |

TABLE IV-continued
ALKYLATION OF BIPHENYL USING VARIOUS ACID-TYPE ALKYLATION CATALYSTS

| Run No. | Catalyst | Reaction Temp. °C. | $C_3^=$/BP Mole Ratio | % BP Conv. | % Selectivity at Various Conversions | | |
|---|---|---|---|---|---|---|---|
| | | | | | 2-IPBP | 3-IPBP | 4-IPBP |
| 6 | AlCl$_3$ + 2.5 mL CS$_2$ per g biphenyl | 80 | .55 | 50 | 0 | 55 | 36 |
| | | 80 | .95 | 75 | 0 | 40 | 25 |
| | | 25 | .62 | 50 | 17 | 32 | 37 |
| | | 25 | 1.33 | 75 | 11 | 23 | 26 |

<sup>a</sup>Davison G979 crushed to a powder
<sup>b</sup>Davison G979 crushed (55 mL), treated with 20 mL of 96% sulfuric acid giving moist powder.
<sup>c</sup>80% Sulfuric acid on Micro-Gel
<sup>d</sup>Linde Mole Sieve (high acidity) 33-511, crushed.

SUMMARY

The data herein disclosed is summarized in Table V wherein it can be seen that when the inventive catalyst, acid-treated montmorillonite and BF$_3$.H$_3$PO$_4$, and perfluorosulfonic acid resin are employed in the alkylation of biphenyl, the major product is the 2-alkylated biphenyl; whereas with the control catalysts the major product is generally the 4-alkylated biphenyl. In addition, the data indicates lower reaction temperatures when the inventive catalysts are employed in the alkylation.

TABLE V
SUMMARY

| EXAMPLE | Catalyst | % Biphenyl Conversion | Optimum Rxn Temp °C. | % Selectivity by GLC Isopropylbiphenyl | | |
|---|---|---|---|---|---|---|
| | | | | 2- | 3- | 4- |
| Invention | | | | | | |
| I | Perfluorosulfonic Acid Polymer (Nafion H) | 50 | 180 | 43 | 14 | 27 |
| | | 75 | 180 | 33 | 9 | 20 |
| II | Acid-Treated Montmorillonite (Filtrol 71) | 4.5 | 100 | 64.8 | 9.7 | 24.7 |
| | | 30.7 | 100 | 59.4 | 11.6 | 24.2 |
| | | 72.4 | 100 | 42.2 | 9.9 | 15.8 |
| III | BF$_3$.H$_3$PO$_4$ | 55.6 | 70 | 36.7 | 16.6 | 29.5 |
| | | 53.1 | 75 | 39.3 | 19.9 | 28. |
| Control: | | | | | | |
| IV | Silica Alumina | 50 | 150 | 29 | 15 | 42 |
| | | 75 | 150 | 21 | 10 | 31 |
| IV | Acid-Treated Silica Alumina | 50 | 155 | 36 | 11 | 33 |
| | | 75 | 180 | 23 | 7 | 25 |
| IV | Acid-Treated Micro-Gel | 44 | 180 | 35 | 9 | 36 |
| IV | High Acid Linde Mole Sieve | 35 | 100 | 46 | 18 | 29 |
| IV | AlCl$_3$ | 50 | 25 | 17 | 22 | 37 |
| | | 75 | 25 | 11 | 23 | 26 |

Reasonable variations, such as those which would occur to the skilled artisan, may be made herein without departing from the scope of the invention.

I claim:

1. A process for the selective production of 2-alkyl-substituted polycyclic aromatic compounds comprising contacting one or more aromatic reactants of the general formula

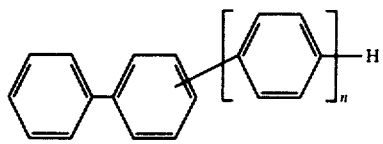

where n can equal 0 or any integer from about 1 to about 4 with at least one 1-olefin and a mole ratio of olefin to aromatic compound ranging from about 0.2:1 to about 2.5:1 at moderate temperatures between about 65° and 135° C. in the presence of a catalyst selected from the group consisting of BF$_3$ complexes, acid-treated clays, and mixtures thereof.

2. The process of claim 1 wherein the molar ratio of 1-olefin to aromatic reactants is between about 0.2:1 and 2.0:1.

3. The process of claim 2 wherein the catalyst is BF$_3$.H$_3$PO$_4$.

4. The process of claim 3 wherein the temperature of alkylation is about 70° C. to about 80° C.

5. The process of claim 1 wherein the catalyst is an acid-treated montmorillonite clay.

6. The process of claim 5 wherein the temperature is about 75° C. to about 125° C.

7. The process of claim 3 wherein the olefin is propylene.

8. The process of claim 7 wherein the aromatic reactant is biphenyl.

9. The process of claim 3 wherein the temperature of reaction is about 70° C. to about 75° C.

10. The process of claim 5 wherein the temperature of reaction is about 100° C. to about 125° C.

11. The process of claim 8 wherein the major reaction product comprises 2-alkylbiphenyls.

12. The process of claim 5 wherein the aromatic reactant is biphenyl and the 1-olefin is propylene.

13. The process of claim 12 wherein the major reaction product comprises 2-alkylbiphenyls.

* * * * *